United States Patent [19]

Bonath et al.

[11] 4,199,529
[45] Apr. 22, 1980

[54] PROCESS FOR THE PRODUCTION OF AMINO-I-ACID

[75] Inventors: Bernt Bonath, Muttenz; Sebastian Stäubli, Magden; Hans Horisberger, Muttenz; Istvan Székely, Basel, all of Switzerland

[73] Assignee: Ciba-Geigy AG, Basel, Switzerland

[21] Appl. No.: 947,291

[22] Filed: Sep. 29, 1978

[30] Foreign Application Priority Data

Oct. 3, 1977 [CH] Switzerland ............... 12048/77

[51] Int. Cl.$^2$ .................. C07C 139/00; C07C 143/60
[52] U.S. Cl. .................................................. 260/508
[58] Field of Search ......................................... 260/508

[56] References Cited

U.S. PATENT DOCUMENTS

| 1,969,189 | 8/1934 | Tinker et al. ................... 260/508 |
| 3,979,445 | 9/1976 | Ross ................................ 260/508 |

FOREIGN PATENT DOCUMENTS

| 2145656 | 4/1972 | Fed. Rep. of Germany ........... 260/508 |
| 17141A | of 1894 | United Kingdom ..................... 260/508 |
| 17141B | of 1894 | United Kingdom ..................... 260/508 |
| 17141C | of 1894 | United Kingdom ..................... 260/508 |

OTHER PUBLICATIONS

Honben/Weyl–"Meth. der Org. Chem", Band IX, pp. 444–446, 474–485, 536–537 (1955).

*Primary Examiner*—Norman Morgenstern
*Attorney, Agent, or Firm*—Sprung, Felfe, Horn, Lynch & Kramer

[57] ABSTRACT

A process for the production of amino-I-acid (2-naphthylamino-5,7-disulfonic acid) starting from Tobias acid (2-naphthylamine-1-sulfonic acid), which comprises sulfonating Tobias acid with fuming sulfuric acid (oleum) isothermically at room temperature, further sulfonating the resulting 2-naphthylamine-1,5-disulfonic acid without isolation, by rapidly heating the reaction mixture to 110° to 140° C. to give 2-naphthylamine-1,5,7-trisulfonic acid, hydrolyzing the trisulfonic acid in sulfuric acid having a concentration between 80 and 98%, at a temperature of 100°–180° C.. to give the amino-I-acid, precipitating this latter from dilute sulfuric acid and isolating it from the reaction mixture, and the amino-I-acid obtained by this process.

5 Claims, 1 Drawing Figure

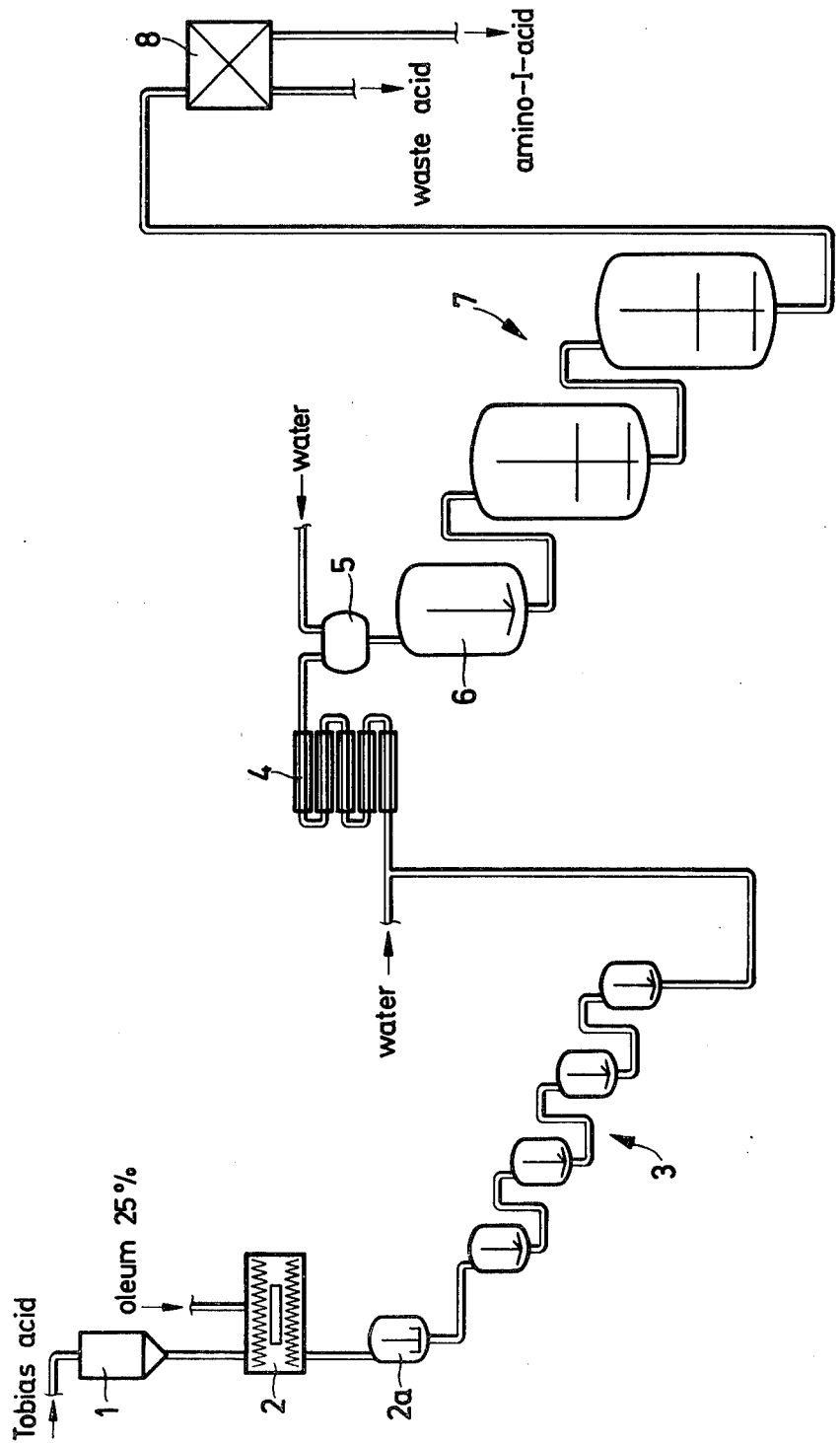

PROCESS FOR THE PRODUCTION OF AMINO-I-ACID

The present invention concerns a novel process for the production of amino-I-acid (2-naphthylamine-5,7-disulfonic acid) starting from Tobias acid (2-naphthylamine-1-sulfonic acid).

The following scheme illustrates the reaction course:

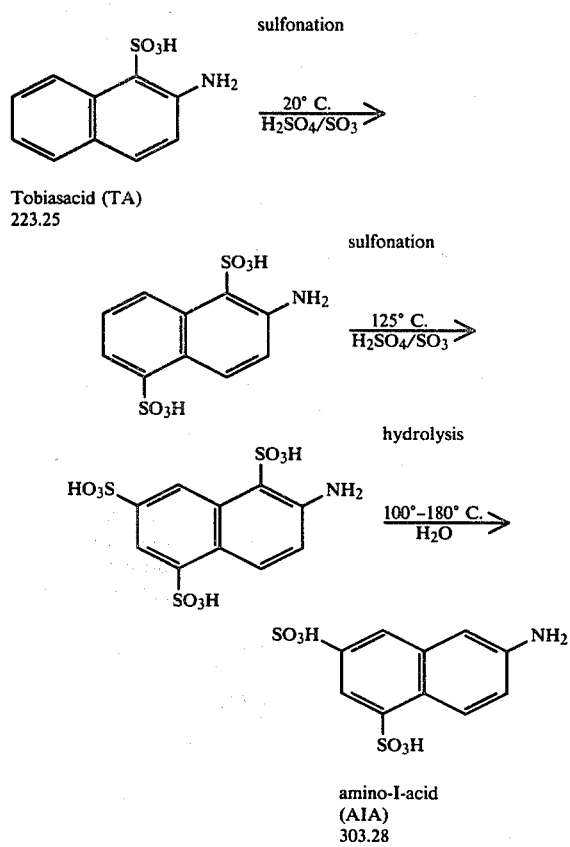

Amino-I-acid is an important dyestuff intermediate. The drawback of the known methods of obtaining it is that amino-I-acid always occurs in admixture with the isomeric amino-G-acid (2-naphthylamino-6,8-disulfonic acid). However, because amino-I-acid of high purity, if possible without any impurities, is required for the manufacture of compatible dyes, expensive cleansing operations, the effectiveness of which is often unsatisfactory, have to be employed in order to separate the mixture.

It is therefore the object of the present invention to provide a novel process which makes it possible to produce amino-I-acid in simple manner and in the required purity and yield employing environmentally clean technology and an energy-saving method.

Surprisingly, it has now been found that the aforementioned drawbacks do not arise when optimising the process conditions, such as the temperature ranges and acid concentrations of the individual reaction steps.

The novel process for the production of amino-I-acid, starting from Tobias acid, comprises sulfonating Tobias acid with fuming sulfuric acid (oleum) isothermically at room temperature, further sulfonating the resulting 2-naphthylamine-1,5-disulfonic acid, without isolation, by rapidly heating the reaction mixture to 110° to 140° C., and maintaining this temperature advantageously for 2 to 5 hours, to give 2-naphthylamine-1,5,7-trisulfonic acid, and, after reducing the sulfuric acid concentration to 80-98% by addition of water at a temperature between 100° and 180° C., hydrolysing the trisulfonic acid to the amino-I-acid, precipitating this latter by diluting the sulfuric acid with water, and isolating it from the reaction mass, for example by filtration.

Preferred temperature ranges of the novel process are between 15° and 25° C. for the sulfonation to give the disulfonic acid, between 120° and 130° C. for the sulfonation to give the trisulfonic acid, and either adiabatic temperatures of 150° to 180° C. or isothermic temperatures of 100° to 130° C. for the hydrolysis. If isothermic hydrolysis is carried out, intensive cooling is necessary. Crystallisation and isolation are advantageously carried out at 20° to 30° C.

The preferred sulfuric acid concentrations in the process of the present invention are: 17 to 27% ($SO_3$ content) oleum for the sulfonation to give the disulfonic acid, 5 to 15% oleum for the sulfonation to give the trisulfonic acid, 90 to 95% sulfuric acid for the hydrolysis, and 40 to 45% sulfuric acid for the crystallisation.

Only the combination of the aforementioned preferred temperature ranges and sulfuric acid concentrations results in optimum yield and purity of the amino-I-acid, for example in a continuous process in the same reactor without isolation of the intermediates.

Further advantages of the process of the invention are a lower consumption of sulfuric acid and advantageous physical properties of the end product, for example the crystal modification. This latter promotes the filtration of the product, with ecologically favourable results. In particular, an automatic pressure filter can be employed for the filtration. A product with, for example, a residual moisture content of less than 40% can only be isolated by complicated filtration methods, for example by centrifuging. On account of the quality of the product obtained by the process of the present invention, the otherwise customary "scaling", which constitutes a complicated and ecologically unsafe cleansing step, is dispensed with.

The process can be carried out continuously or discontinuously. The reaction times are relatively short in accordance with the process conditions, whereby a continuous mode of operation has really only been made possible. In the continuous mode of operation, the procedure can for example be as follows in accordance with the attached diagram:

From the silo 1, dry Tobias acid is charged proportionally with 25% oleum (about 2.4 mol/mol of TA) by means of solid addition into a reactor 2. The Tobias acid is wetted therein, homogenised, and the heat of reaction is drawn off. The reaction mass overflows into the agitator vessel 2a until the disulfonation is complete. The disulfonation is carried out isothermically at about 20° C. and takes about 30 minutes. The trisulfonation is carried out in the descending series of agitator vessels 3 in the same reaction medium by means of rapid or programmed temperature increase to 120° C., whereupon the mixture is stirred for 2 to 5 hours. To effect hydrolysis and crystallisation, the trisulfonation mixture is pumped into the mixer 4. The acid concentration is adjusted to about 90% by proportional addition of water and the temperature to about 130° C. by cooling. In the continous agitator vessel 5 the reaction mass is diluted at a temperature of 100° C. with water to the optimum acid concentration of about 45% for the crystallisation. To effect crystallisation, the reaction mass is abruptly cooled to 30° C. in the vessel 6. Subsequent precipitation takes place in the vessel 7 at 20° to 30° C. The amino-I-acid is isolated on the automatic pressure filter 8. It can be further processed moist or can be dried.

The waste acid occurring as mother liquor can be used in the production of other "letter acids", for example by neutralisation, whereby no wastewater results.

The novel process has economic advantages especially on account of the high space-time yields, the simple procedure and the purity of the end product.

The amino-I-acid obtained by the process of the invention can be reacted, for example by fusion with NaOH, to give I-acid, which is widely used as coupling and condensation component in dyestuff synthesis. By way of example, mention may be made of the synthesis of the fibre-reactive indicator dyes disclosed in German Offenlegungsschrift No. 2,362,859, wherein the I-acid undergoes a coupling and condensation reaction. Further use examples are to be found in German Offenlegungsschrift No. 2,215,081, Japanese published patent specification No. 73-32855, German Offenlegungsschrift No. 2,503,653 and U.S. Pat. No. 3,928,778.

In the following Example the parts are by weight.

EXAMPLE OF THE DISCONTINUOUS METHOD (a) Disulfonation

A 500 ml double mantle flask with bottom outlet and equipped with a steel hook stirrer is charged with 104.6 g (1.31 moles) of 100% $SO_3$ as 25% oleum (80.07). With stirring, 121.8 g (0.545 mole) of Tobias acid (99–100%) are added in the course of half an hour via the addition means. The reaction temperature is kept for 30 minutes at 20° C. ($\pm 2°$ C.) by cooling in the double mantle.

(b) Trisulfonation

The disulfonation mixture of (a) is heated to 120° C. for 15 minutes in a 1½ liter four-necked flask equipped with steel hook stirrer, reflux cooler with drying tube and $SO_3$ absorption means as well as thermometer, and kept for 3½ hours at 125° C. with stirring. The mixture is thereafter cooled to room temperature (to about 60° C. in the continuous method).

(c) Hydrolysis

With stirring (150 rpm), 490 g of deionised water are added to the trisulfonation mixture of (b) from a dropping funnel in the course of about 15 minutes. The hydrolysis is effected during the first half of the addition of water. The reaction is strongly exothermic. The internal temperature increases rapidly and is held at about 110° C. by cooling with an ice-water bath and allowed to rise to 117° C. The remainder of the water is added at 115°–117° C. with heating. Subsequently, the internal temperature is allowed to fall to about 110° C. and kept at this temperature for 1 hour with stirring. The batch is then allowed to cool slowly to room temperature for several hours with stirring, and, if desired or necessary, stirring is continued for a time until the formation of the desired crystal modification. The crystalline amino-I-acid is filtered off with suction. Depending on the end-use requirement, it is further processed in the moist state or as a solution or dried. Yield: 132.3 g of amino-I-acid (80% of theory). Purity: at least 90%.

What is claimed is:

1. A process for the production of amino-I-acid (2-naphthylamino-5,7-disulfonic acid) starting from Tobias acid (2-naphthylamine-1-sulfonic acid), which comprises sulfonating Tobias acid with fuming sulfuric acid (oleum) isothermically at room temperature, further sulfonating the resulting 2-naphthylamine-1,5-disulfonic acid without isolation, by rapidly heating the reaction mixture to 110° to 140° C. to give 2-naphthylamine-1,5,7-trisulfonic acid, hydrolysing the trisulfonic acid in sulfuric acid having a concentration between 80 and 98%, at a temperature of 100°–180° C., to give the amino-I-acid, precipitating this latter from dilute sulfuric acid and isolating it from the reaction mixture.

2. A process according to claim 1, wherein the sulfonation to give the disulfonic acid is carried out in 17 to 27% oleum ($SO_3$ content), the sulfonation to give the trisulfonic acid is carried out in 5 to 15% oleum, the hydrolysis is carried out in 90 to 95% sulfuric acid and the crystallisation is effected from 40 to 45% sulfuric acid.

3. A process according to any one of claims 1 and 2, wherein the sulfonation to give the disulfonic acid is carried out at a temperature between 15° and 25° C., the sulfonation to give the trisulfonic acid at a temperature between 120° and 130° C., the hydrolysis is carried out isothermically at a temperature between 100° and 130° C. or adiabatically at a temperature between 150° and 180° C., and the crystallisation and isolation are carried out at a temperature between 20° and 30° C.

4. A process according to any one of claims 1 to 3, wherein the amino-I-acid is isolated by filtration on an automatic pressure filter.

5. A process according to any one of claims 1 to 4, wherein the process is carried out continuously.

* * * * *